(12) United States Patent
McGuckin, Jr. et al.

(10) Patent No.: US 7,909,847 B2
(45) Date of Patent: *Mar. 22, 2011

(54) VEIN FILTER

(75) Inventors: James F. McGuckin, Jr., Radnor, PA (US); John H. Thinnes, Jr., Miami Beach, FL (US)

(73) Assignee: Rex Medical, L.P., Conshohocken, PA (US)

( * ) Notice: Subject to any disclaimer, the term of this patent is extended or adjusted under 35 U.S.C. 154(b) by 579 days.

This patent is subject to a terminal disclaimer.

(21) Appl. No.: 11/219,433

(22) Filed: Sep. 2, 2005

(65) Prior Publication Data

US 2007/0088381 A1 Apr. 19, 2007

(51) Int. Cl.
*A61M 29/00* (2006.01)
(52) U.S. Cl. .......... 606/200; 606/106; 606/107
(58) Field of Classification Search .......... 606/198, 606/200
See application file for complete search history.

(56) References Cited

U.S. PATENT DOCUMENTS

| | | |
|---|---|---|
| 3,744,492 A | 7/1973 | Leibinsohn |
| 3,952,747 A | 4/1976 | Kimmel, Jr. |
| 4,425,908 A | 1/1984 | Simon |
| 4,494,531 A | 1/1985 | Gianturco |
| 4,512,338 A | 4/1985 | Balko et al. |
| 4,619,246 A | 10/1986 | Molgaard-Nielsen et al. |
| 4,643,184 A * | 2/1987 | Mobin-Uddin ............... 606/200 |
| 4,688,553 A | 8/1987 | Metals |
| 4,727,873 A | 3/1988 | Mobin-Uddin |
| 4,781,177 A * | 11/1988 | Lebigot .......................... 128/897 |
| 4,793,348 A | 12/1988 | Palmaz |
| 4,817,600 A | 4/1989 | Herms et al. |
| 4,832,055 A * | 5/1989 | Palestrant ..................... 128/899 |
| 4,957,501 A | 9/1990 | Lahille et al. |
| 4,990,156 A | 2/1991 | Lefebvre |
| 4,994,069 A | 2/1991 | Ritchart et al. |
| 5,059,205 A | 10/1991 | El-Nounou et al. |
| 5,133,733 A | 7/1992 | Rasmussen et al. |
| 5,152,777 A | 10/1992 | Goldberg et al. |
| 5,234,458 A | 8/1993 | Metals |
| 5,300,086 A | 4/1994 | Gory et al. |
| 5,324,304 A | 6/1994 | Rasmussen |
| 5,344,427 A | 9/1994 | Cottenceau et al. |

(Continued)

FOREIGN PATENT DOCUMENTS

DE 3429850 2/1986

(Continued)

OTHER PUBLICATIONS

Braun Medical, Inc. Vena Tech™ Vena Cava Filters, Feb. 2000.

(Continued)

*Primary Examiner* — Anhtuan T Nguyen
*Assistant Examiner* — Julie A Szpira
(74) *Attorney, Agent, or Firm* — Neie D. Gershon

(57) ABSTRACT

A vessel filter having a first region having a first set of struts forming a mounting portion and a filter portion having a converging region at a first portion to direct particles toward the center of the filter. The mounting portion is flared in the expanded position to have a transverse dimension increasing toward a second portion opposite the first portion. A second set of struts forms a second mounting portion flared in the expanded position. A plurality of spaced apart struts extend between the first and second regions.

20 Claims, 8 Drawing Sheets

U.S. PATENT DOCUMENTS

| | | | |
|---|---|---|---|
| 5,350,398 A | 9/1994 | Pavcnik et al. | |
| 5,370,657 A | 12/1994 | Irie | |
| 5,375,612 A | 12/1994 | Cottenceau et al. | |
| 5,382,261 A | 1/1995 | Palmaz | |
| 5,383,887 A | 1/1995 | Nadal | |
| 5,405,377 A | 4/1995 | Cragg | |
| 5,531,788 A | 7/1996 | Dibie et al. | |
| 5,591,197 A | 1/1997 | Orth et al. | |
| 5,601,595 A | 2/1997 | Smith | |
| 5,626,605 A | 5/1997 | Irie et al. | |
| 5,634,942 A | 6/1997 | Chevillon et al. | |
| 5,681,347 A | 10/1997 | Catheart et al. | |
| 5,683,411 A | 11/1997 | Kavteladze et al. | |
| 5,690,671 A | 11/1997 | McGurk et al. | |
| 5,709,704 A | 1/1998 | Nott et al. | |
| 5,725,552 A | 3/1998 | Kotula et al. | |
| 5,733,294 A | 3/1998 | Forber et al. | |
| 5,733,329 A | 3/1998 | Wallace et al. | |
| 5,746,767 A | 5/1998 | Smith | |
| 5,755,779 A | 5/1998 | Horiguchi | |
| 5,755,790 A | 5/1998 | Chevillon et al. | |
| 5,776,162 A | 7/1998 | Kleshinski | |
| 5,782,748 A | 7/1998 | Palmer et al. | |
| 5,795,322 A | 8/1998 | Boudewijn | |
| 5,810,874 A | 9/1998 | Lefebvre | |
| 5,836,968 A * | 11/1998 | Simon et al. | 606/200 |
| 5,853,420 A | 12/1998 | Chevillon et al. | |
| 5,893,869 A | 4/1999 | Barnhart et al. | |
| 5,895,398 A | 4/1999 | Wensel et al. | |
| 5,895,410 A | 4/1999 | Forber et al. | |
| 5,911,717 A | 6/1999 | Jacobsen et al. | |
| 5,968,071 A | 10/1999 | Chevillon et al. | |
| 5,976,172 A | 11/1999 | Homsma et al. | |
| 5,984,947 A | 11/1999 | Smith | |
| 6,007,558 A | 12/1999 | Ravenscroft et al. | |
| 6,013,093 A | 1/2000 | Nott et al. | |
| 6,042,598 A | 3/2000 | Tsugita et al. | |
| 6,059,825 A | 5/2000 | Hobbs et al. | |
| 6,063,113 A | 5/2000 | Kavteladze et al. | |
| 6,066,158 A | 5/2000 | Engelson et al. | |
| 6,080,178 A | 6/2000 | Meglin | |
| 6,093,196 A | 7/2000 | Okada | |
| 6,093,199 A | 7/2000 | Brown et al. | |
| 6,096,052 A | 8/2000 | Callister et al. | |
| 6,099,549 A | 8/2000 | Bosma et al. | |
| 6,117,154 A | 9/2000 | Barbut et al. | |
| 6,123,715 A | 9/2000 | Amplatz | |
| 6,126,673 A | 10/2000 | Kim et al. | |
| 6,146,404 A | 11/2000 | Kim et al. | |
| 6,152,946 A | 11/2000 | Broome et al. | |
| 6,165,179 A | 12/2000 | Cathcart et al. | |
| 6,165,198 A | 12/2000 | McGurk et al. | |
| 6,168,579 B1 | 1/2001 | Tsugita | |
| 6,168,603 B1 | 1/2001 | Leslie et al. | |
| 6,171,327 B1 | 1/2001 | Daniel et al. | |
| 6,171,328 B1 | 1/2001 | Addis | |
| 6,179,851 B1 | 1/2001 | Barbut et al. | |
| 6,179,859 B1 | 1/2001 | Bates et al. | |
| 6,187,025 B1 | 2/2001 | Machek | |
| 6,193,739 B1 | 2/2001 | Chevillon et al. | |
| 6,214,025 B1 | 4/2001 | Thistle et al. | |
| 6,217,600 B1 | 4/2001 | DiMatteo | |
| 6,231,581 B1 | 5/2001 | Shank et al. | |
| 6,231,589 B1 * | 5/2001 | Wessman et al. | 606/200 |
| 6,235,044 B1 | 5/2001 | Root et al. | |
| 6,235,045 B1 | 5/2001 | Barbut et al. | |
| 6,241,746 B1 | 6/2001 | Bosma et al. | |
| 6,245,012 B1 | 6/2001 | Kleshinski | |
| 6,251,122 B1 | 6/2001 | Tsukernik | |
| 6,258,026 B1 | 7/2001 | Ravenscroft et al. | |
| 6,267,776 B1 | 7/2001 | O'Connell | |
| 6,273,901 B1 | 8/2001 | Whitcher et al. | |
| 6,280,451 B1 | 8/2001 | Bates et al. | |
| 6,280,457 B1 | 8/2001 | Wallace et al. | |
| 6,290,721 B1 | 9/2001 | Heath | |
| 6,328,755 B1 | 12/2001 | Marshall | |
| 6,331,184 B1 | 12/2001 | Abrams | |
| 6,342,062 B1 | 1/2002 | Suon et al. | |
| 6,342,063 B1 | 1/2002 | Devries et al. | |
| 6,344,041 B1 | 2/2002 | Kupiecki et al. | |
| 6,355,051 B1 * | 3/2002 | Sisskind et al. | 606/200 |
| 6,368,338 B1 | 4/2002 | Konya et al. | |
| 6,383,205 B1 | 5/2002 | Samson et al. | |
| 6,391,045 B1 * | 5/2002 | Kim et al. | 606/200 |
| 6,402,771 B1 | 6/2002 | Palmer et al. | |
| 6,436,120 B1 | 8/2002 | Meglin | |
| 6,436,121 B1 | 8/2002 | Blom | |
| 6,443,971 B1 | 9/2002 | Boylan et al. | |
| 6,443,972 B1 | 9/2002 | Bosma et al. | |
| 6,447,530 B1 | 9/2002 | Ostrovsky et al. | |
| 6,447,531 B1 | 9/2002 | Amplatz | |
| 6,458,139 B1 | 10/2002 | Palmer et al. | |
| 6,468,290 B1 | 10/2002 | Weldon et al. | |
| 6,482,222 B1 | 11/2002 | Bruckheimer et al. | |
| 6,506,205 B2 | 1/2003 | Goldberg et al. | |
| 6,517,559 B1 | 2/2003 | O'Connell | |
| 6,527,962 B1 | 3/2003 | Nadal | |
| 6,537,294 B1 | 3/2003 | Boyle et al. | |
| 6,540,767 B1 | 4/2003 | Walak et al. | |
| 6,551,342 B1 | 4/2003 | Shen et al. | |
| 6,562,058 B2 | 5/2003 | Sequin et al. | |
| 6,599,307 B1 | 7/2003 | Huter et al. | |
| 6,605,102 B1 | 8/2003 | Mazzocchi et al. | |
| 6,620,183 B2 * | 9/2003 | DiMatteo | 606/202 |
| 6,652,558 B2 | 11/2003 | Patel et al. | |
| 6,656,202 B2 | 12/2003 | Papp et al. | |
| 6,660,021 B1 | 12/2003 | Palmer et al. | |
| 6,695,878 B2 | 2/2004 | McGuckin et al. | |
| 6,783,538 B2 | 8/2004 | McGuckin et al. | |
| 6,793,665 B2 | 9/2004 | McGuckin et al. | |
| 6,890,340 B2 | 5/2005 | Duane | |
| 6,932,831 B2 | 8/2005 | Forber | |
| 6,958,074 B2 | 10/2005 | Russell | |
| 6,972,025 B2 | 12/2005 | WasDyke | |
| 6,989,021 B2 | 1/2006 | Bosma et al. | |
| 6,994,092 B2 | 2/2006 | van der Burg et al. | |
| 7,037,321 B2 | 5/2006 | Sachdeva et al. | |
| 7,097,651 B2 | 8/2006 | Harrison et al. | |
| 7,232,462 B2 | 6/2007 | Schaeffer et al. | |
| 7,279,000 B2 | 10/2007 | Cartier et al. | |
| 7,316,708 B2 | 1/2008 | Gordon et al. | |
| 2002/0058911 A1 | 5/2002 | Gilson et al. | |
| 2002/0116024 A1 | 8/2002 | Goldberg et al. | |
| 2002/0193827 A1 | 12/2002 | McGuckin et al. | |
| 2002/0193828 A1 | 12/2002 | Griffin et al. | |
| 2003/0130680 A1 | 7/2003 | Russell | |
| 2003/0195555 A1 | 10/2003 | Khairkhahan et al. | |
| 2003/0208227 A1 | 11/2003 | Thomas | |
| 2003/0208253 A1 | 11/2003 | Beyer et al. | |
| 2004/0044361 A1 | 3/2004 | Frazier et al. | |
| 2004/0073252 A1 | 4/2004 | Goldberg et al. | |
| 2004/0088001 A1 * | 5/2004 | Bosma et al. | 606/200 |
| 2004/0093017 A1 | 5/2004 | Chanduszko | |
| 2004/0186510 A1 | 9/2004 | Weaver | |
| 2004/0215230 A1 | 10/2004 | Frazier et al. | |
| 2004/0230220 A1 | 11/2004 | Osborne | |
| 2005/0004596 A1 | 1/2005 | McGuckin et al. | |
| 2005/0015111 A1 | 1/2005 | McGuckin et al. | |
| 2005/0027314 A1 | 2/2005 | WasDyke | |
| 2005/0043757 A1 | 2/2005 | Arad et al. | |
| 2005/0165442 A1 | 7/2005 | Thinnes et al. | |
| 2005/0182439 A1 | 8/2005 | Lowe | |
| 2005/0234503 A1 | 10/2005 | Ravenscroft et al. | |
| 2005/0251199 A1 | 11/2005 | Osborne et al. | |
| 2005/0267514 A1 | 12/2005 | Osborne et al. | |
| 2005/0288704 A1 | 12/2005 | Cartier et al. | |
| 2006/0030875 A1 | 2/2006 | Tessmer | |
| 2006/0058832 A1 | 3/2006 | Melzer et al. | |
| 2006/0069406 A1 | 3/2006 | Hendriksen et al. | |
| 2006/0079928 A1 | 4/2006 | Cartier et al. | |
| 2006/0100660 A1 | 5/2006 | Osborne et al. | |
| 2006/0106417 A1 | 5/2006 | Tessmer et al. | |
| 2006/0178695 A1 | 8/2006 | Decant et al. | |
| 2006/0206138 A1 | 9/2006 | Eidenschink | |
| 2007/0005095 A1 | 1/2007 | Osborne et al. | |
| 2007/0032816 A1 | 2/2007 | O'Connell et al. | |
| 2007/0173885 A1 | 7/2007 | Cartier et al. | |

FOREIGN PATENT DOCUMENTS

| | | |
|---|---|---|
| EP | 1707233 | 10/2006 |
| FR | 2567405 | 1/1986 |
| WO | WO 9312723 | 7/1993 |
| WO | WO 9509567 | 4/1995 |
| WO | WO 9925252 | 5/1999 |
| WO | WO 0145590 | 6/2001 |
| WO | WO 0162184 | 8/2001 |
| WO | WO 0172239 | 10/2001 |
| WO | 0211812 | 2/2002 |
| WO | WO03063732 | 8/2003 |
| WO | WO2004049973 | 6/2004 |
| WO | WO 2005034764 | 4/2005 |
| WO | 2005 117750 | 12/2005 |
| WO | 2006 036457 | 4/2006 |

OTHER PUBLICATIONS

Gianturco-Roehm, Bird's Nest® Vena Cava Filter.

Cordis Corporation, TrapEase™ Permanent Vena Cava Filter, "A Small, Easy and Verstaile System for Optimal Pulmonary Emboli Prevention", 2000 (4 pages).

\* cited by examiner

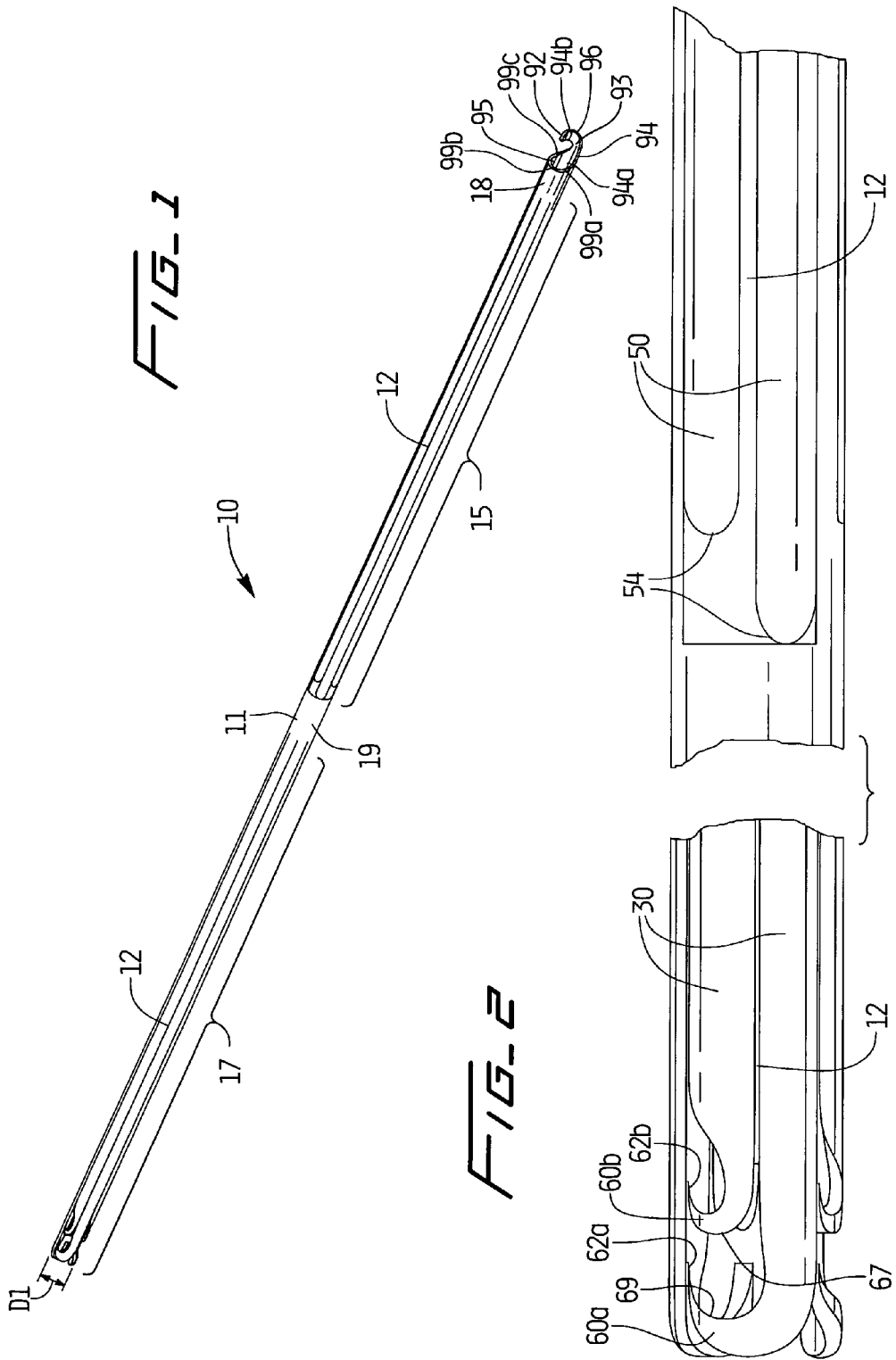

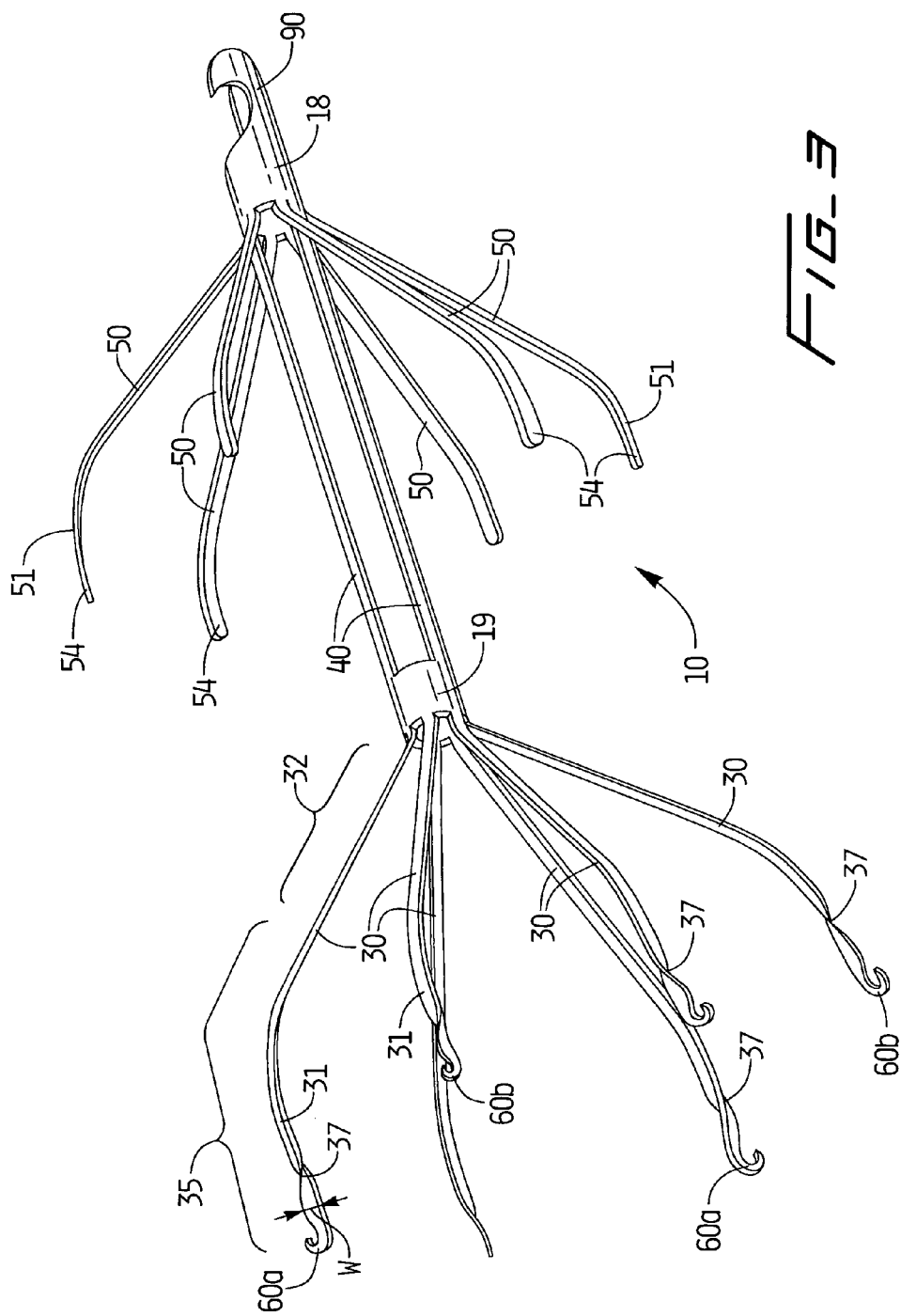

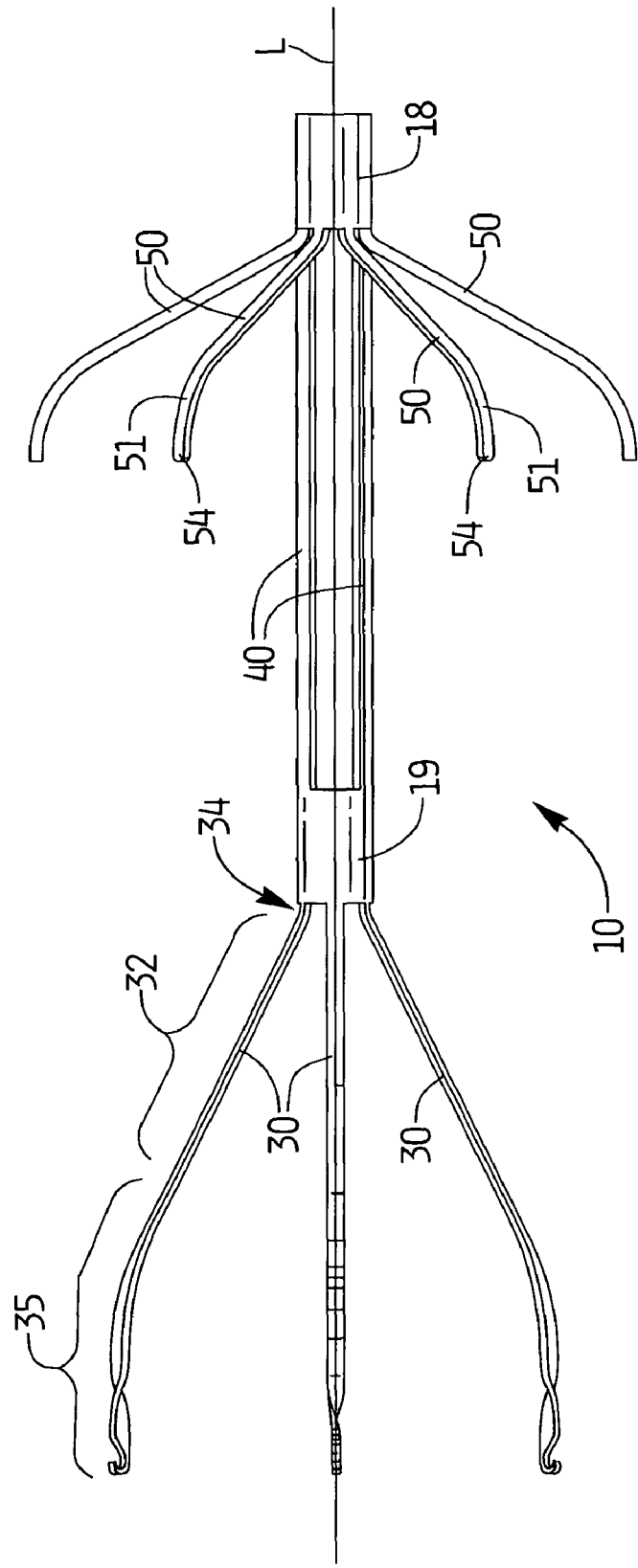

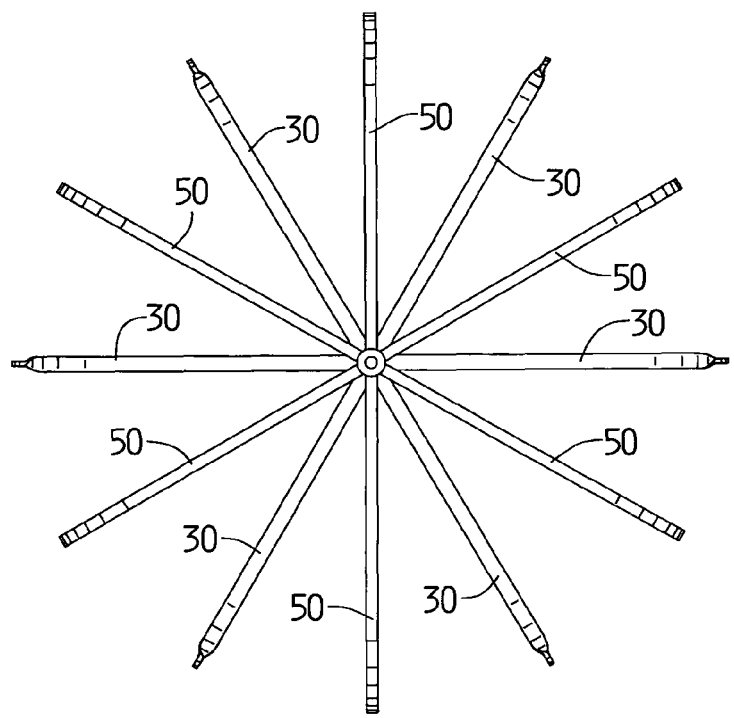
FIG_5A
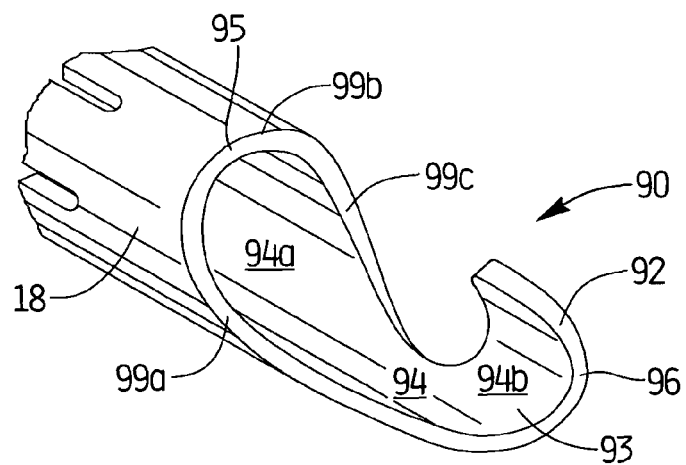
FIG_5B

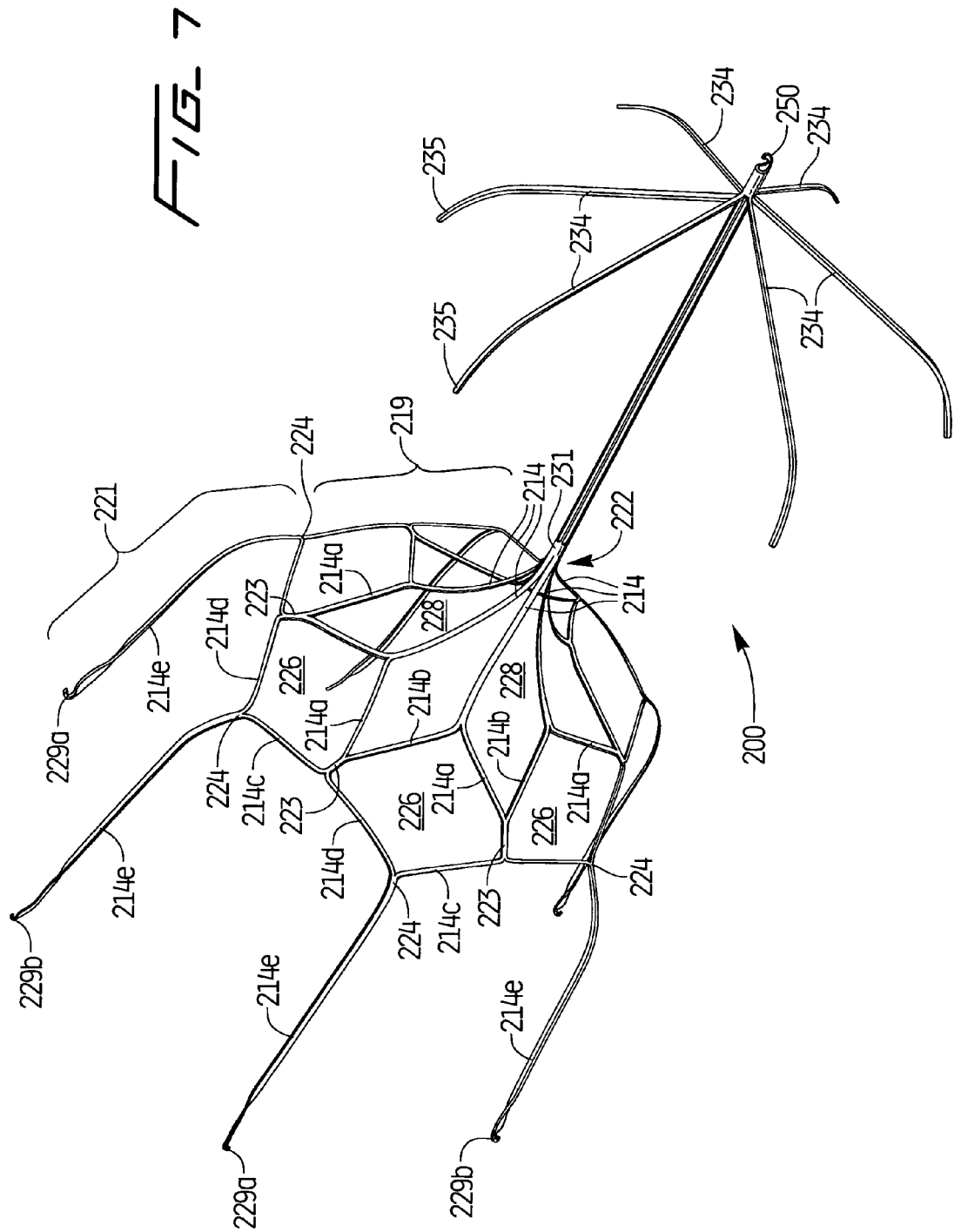

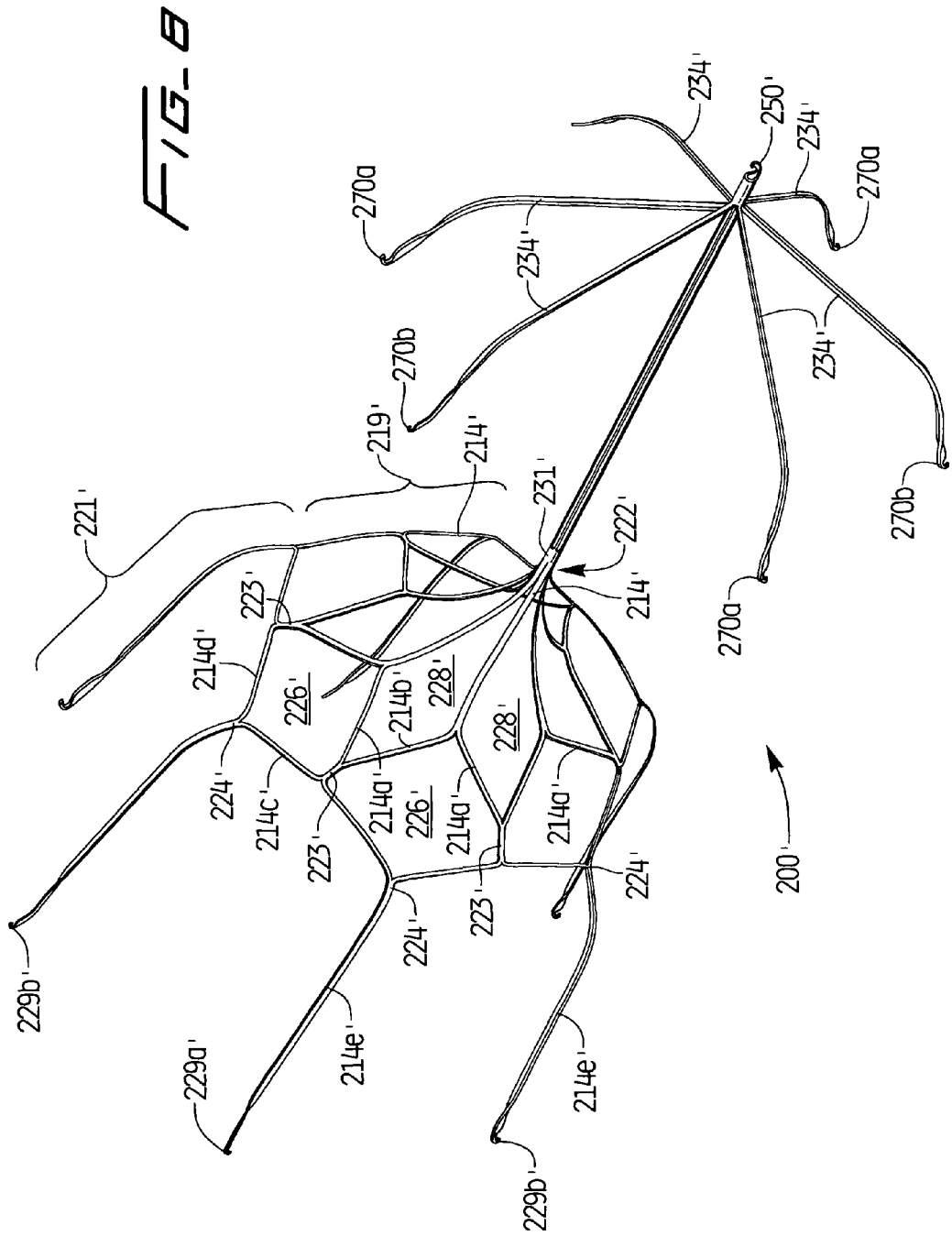

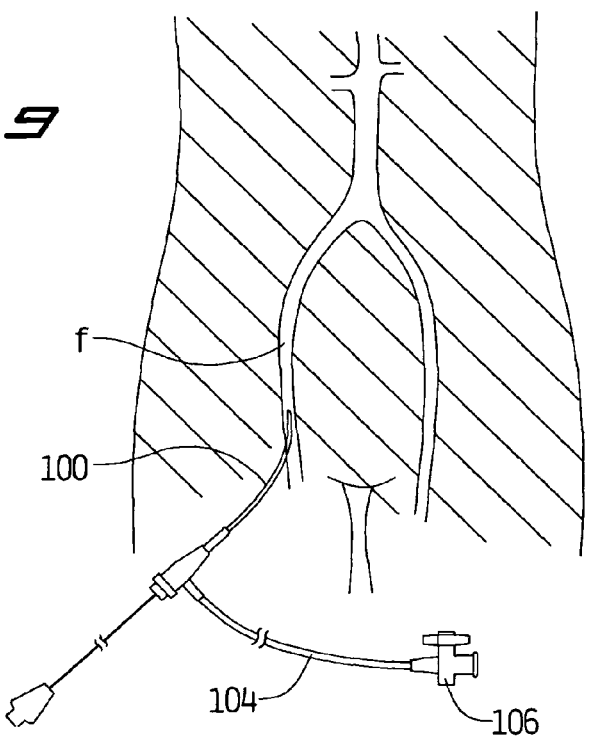
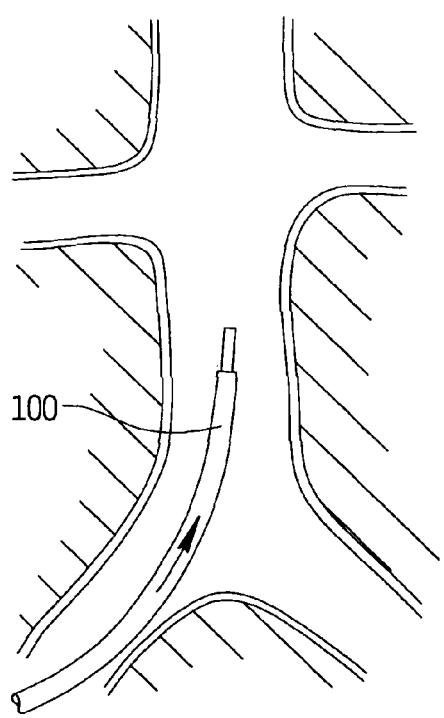
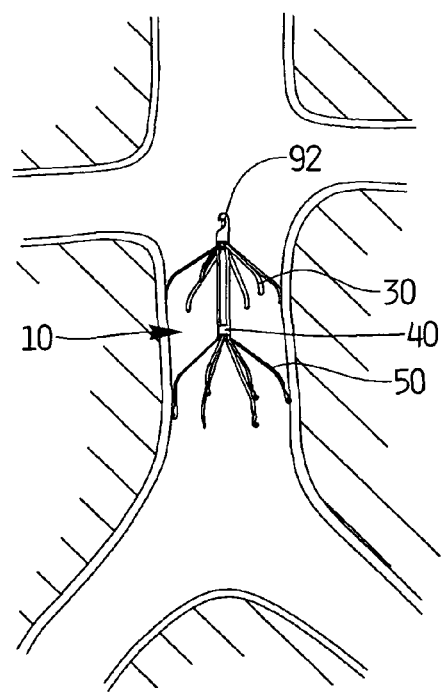

VEIN FILTER

BACKGROUND

1. Technical Field

This application relates to a vascular filter and more particularly to a vein filter for capturing blood clots within the vessel.

2. Background of Related Art

Passage of blood clots to the lungs is known as pulmonary embolism. These clots typically originate in the veins of the lower limbs and can migrate through the vascular system to the lungs where they can obstruct blood flow and therefore interfere with oxygenation of the blood. Pulmonary embolisms can also cause shock and even death.

In some instances, blood thinning medication, e.g. anticoagulants such as Heparin, or sodium warfare can be given to the patient. These medications, however, have limited use since they may not be able to be administered to patients after surgery or stroke or given to patients with high risk of internal bleeding. Also, this medication approach is not always effective in preventing recurring blood clots.

Therefore, surgical methods to reduce the likelihood of such pulmonary embolisms by actually blocking the blood clot from reaching the lungs have been developed. One surgical method of treatment involved major surgery where the size of the vessel lumen was restricted by placement of ligatures or clips around the vein, e.g. the inferior vena cava which transports blood from the lower portion of the body to the heart and lungs. This prevented passage of dangerously large blood clots through the vein to the lungs. However, this approach is an invasive surgical procedure, requiring an abdominal incision and general anesthesia and frequently causing vessel thrombosis and lower extremity swelling. Also, there is a lengthy patient recovery time and additional hospital and surgeon expenses associated with this major surgery. In fact, oftentimes, the patients requiring the surgery are unhealthy and the major surgery and general anesthesia poses a risk in and of itself.

To avoid such invasive surgery, less invasive surgical techniques have been developed. These involve the placement of a mechanical barrier in the inferior vena cava. These barriers are in the form of filters and are typically inserted through either the femoral vein in the patient's leg or the right jugular vein in the patient's neck or arm under local anesthesia. The filters are then advanced intravascularly to the inferior vena cava where they are expanded to block migration of the blood clots from the lower portion of the body to the heart and lungs.

These prior filters take various forms. One type of filter is composed of coiled wires such as disclosed in U.S. Pat. Nos. 5,893,869 and 6,059,825. Another type of filter consists of legs with free ends having anchors for embedding in the vessel wall to hold the filter. These filters are disclosed, for example, in U.S. Pat. Nos. 4,688,553, 4,781,173, 4,832,055, and 5,059,205, 5,984,947 and 6,007,558. Another type of filter is disclosed in U.S. Pat. No. 6,214,025 consisting of wires twisted together to form a cylindrical anchoring portion conforming to the inner vessel wall surface to exert a radial force and a conical filtering portion.

Several factors have to be considered in designing vein filters. One factor is that the filter needs to be securely anchored within the vessel wall, while avoiding traumatic engagement and damage to the wall as well as damage to the neighboring abdominal aorta. Another factor is that the filter must be collapsible to a sufficiently small size to be easily maneuvered and atraumatically advanced intravascularly to the inferior vena cava or other target vessel. Thirdly, the filter should direct the blood clots to the center of the vessel to improve dissolution of the clot within the vessel by the blood flow.

It would be advantageous to provide a vein filter that satisfies the foregoing parameters. Namely, such vein filter would advantageously have sufficient anchoring force to retain the filter within the vessel while providing atraumatic contact with the vessel wall, would have a minimized insertion (collapsed) profile to facilitate delivery through the vascular system to the surgical site, and would enable migration of the captured blood clots to the center of the vessel. Moreover, it would also be advantageous to provide a filter that could simplify insertion through the femoral or the right jugular vein or arm into the inferior vena cava.

Additionally, the need for a vein filter in many patients is temporary. In these instances it would be advantageous to provide a vein filter that satisfies the foregoing factors and in addition could be readily removed from the patient. It would further be advantageous if the filter could be removed minimally invasively, e.g. intravascularly.

SUMMARY

The present invention overcomes the problems and deficiencies of the prior art. The present invention provides a vessel filter movable between a collapsed position for delivery to the vessel and an expanded position for placement within the vessel. The first region of the filter has a first set of struts forming a first mounting portion and a first filter portion opening in a first direction. The filter portion has a converging region at a first portion to direct particles toward the center of the filter and the mounting portion is flared in the expanded position to have a transverse dimension increasing toward a second portion opposite the first portion. The second region has a second set of struts forming a second mounting portion flared in the expanded position and opening in the first direction. A plurality of spaced apart struts extend between the first and second regions.

In one embodiment, one or more of the struts terminates in a vessel engaging hook. In one embodiment, the filter is formed from a laser cut tube and composed of shape memory material. In one embodiment, adjacent struts of the filter portion of the first set of struts are interconnected.

In one embodiment, the second region includes a retrieval region including a hook having a cutout exposing an internal annular surface dimensioned to receive a portion of a retrieval sheath.

The present invention also provides a vessel filter comprising a body, cut from a tube, having a first region and a second region and movable between a collapsed position for delivery to the vessel and an expanded position for placement within the vessel. The first region of the filter has a first set of spaced apart struts forming a first filter portion having a first converging region and a first mounting region for mounting the filter. The second region is formed by a second set of spaced apart struts forming a second mounting region for mounting the filter. The second set of struts are positioned distal of the first set of struts. The first and second set of struts are connected by at least one longitudinally extending strut and both sets of struts are oriented in a first direction.

One or more of the struts may include vessel engaging members to enhance retention of the filter. In one embodiment, adjacent struts are joined by a connecting strut.

The present invention also provides a vessel filter movable between a collapsed position for delivery to the vessel and an expanded position for placement within the vessel. The first region has a first set of struts having a first mounting portion and a first filter portion opening in a first direction and having a first converging region at a first portion to direct particles toward the center of the filter. The second region has a second set of struts having a second mounting portion. Adjacent struts of the first set of struts are interconnected by strut portions extending towards one another. In one embodiment, struts of the first set of struts terminate in vessel engaging members.

BRIEF DESCRIPTION OF THE DRAWINGS

Preferred embodiment(s) of the present disclosure are described herein with reference to the drawings wherein:

FIG. 1 is a perspective view of a first embodiment of the vein filter of the present invention in the collapsed configuration;

FIG. 2 is an enlarged side view of a portion of the vein filter of FIG. 1;

FIG. 3 is a perspective view of the vein filter of FIG. 1 in an expanded configuration;

FIG. 4 is a side view of the vein filter of FIG. 3 in the expanded configuration;

FIG. 5A is a front view of the vein filter of FIG. 3 in the expanded configuration;

FIG. 5B is an enlarged view of the retrieval hook of FIG. 1;

FIG. 7 is a perspective view of another alternate embodiment of the vein filter of the present invention shown in the expanded configuration;

FIG. 8 is a perspective view of another alternate embodiment of the vein filter of the present invention shown in the expanded configuration; and FIGS. 9, 10, and 11 illustrate delivery and placement of the vessel filter of FIG. 1 in the inferior vena cava wherein FIG. 9 illustrates initial insertion of the delivery sheath through the femoral vein, FIG. 10 illustrates the delivery sheath being advanced toward the inferior vena cava just below (upstream) the juncture of the renal arteries; and FIG. 11 illustrates the delivery sheath fully withdrawn to place the filter in the expanded placement configuration in the inferior vena cava.

DETAILED DESCRIPTION OF PREFERRED EMBODIMENTS

Figure 6:
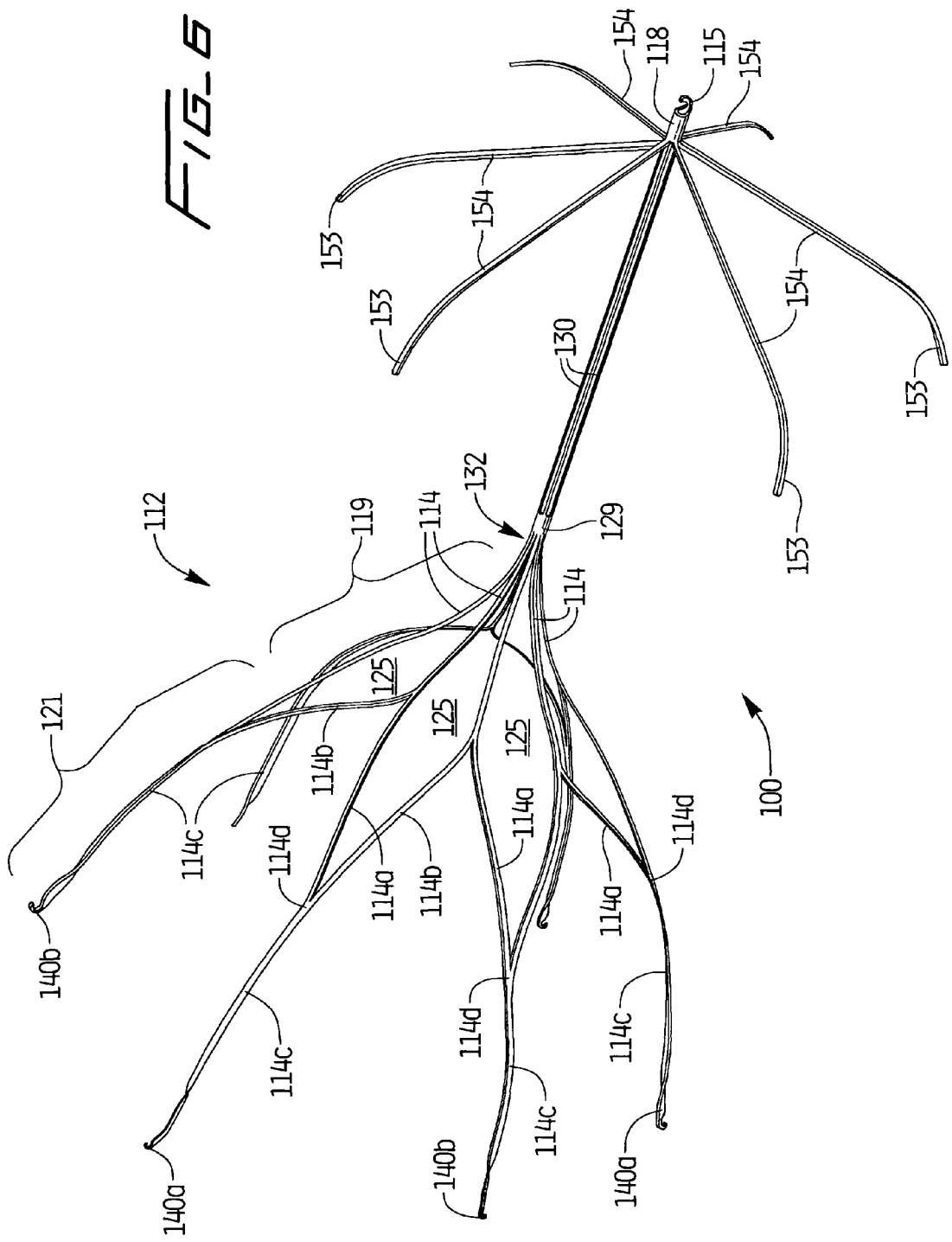
FIG. 6 is a perspective view of an alternate embodiment of the vein filter of the present invention shown in the expanded configuration.

Turning now to the drawings, wherein like reference numerals identify similar or like components throughout the several views, the vein filter of the present invention is described for placement within the inferior vena cava to capture blood clots or other particles which could otherwise pass to the lungs.

The filter is movable from a low profile collapsed configuration to facilitate insertion through the delivery sheath to a larger expanded placement configuration to enable atraumatic engagement with the vessel walls to secure (mount) the filter within the inferior vena cava. The filter has a substantially bell-shaped region having a filtering region (portion/section) and a flared mounting (anchoring) region (portion/section). As described in more detail below, the filtering portion has inwardly directed struts, terminating in a converging region, thereby directing particles toward the central axis of the filter. By directing the particles to the center and trapping them at the center, they will be exposed to greater blood flow than if trapped at the edges of the filter, thereby improving dissolution of the particles. The flared mounting portion provides less contact area than a straight region, resulting in less tissue ingrowth to facilitate removal of the filter if desired. The flare also reduces the chance of vessel distortion if inserted into a curved vena cava. To enhance mounting of the filter, a second mounting region is provided axially spaced from the bell-shaped region. This second region provides a stabilizing portion to help center the filter and limit tilting.

Turning now to the details of the filter of a first embodiment of the present invention and with initial reference to FIGS. 1 and 2, the filter is designated generally by reference numeral 10 and is shown in a collapsed configuration for delivery. Filter 10 is preferably formed from a single tube 11. In a preferred embodiment, the filter 10 is composed of shape memory material, such as Nitinol, a nickel titanium alloy, or elgiloy; however, other materials such as stainless steel are also contemplated. A plurality of cutouts 12 are formed in the filter 10, preferably by laser cutting although other techniques are contemplated. In the illustrated embodiment, six elongated cutouts are formed in the first region 15 and in the second region 17, creating two pairs of six strips or struts 30, 50, respectively, separated by the cutouts 12. Preferably, the struts in each set are of substantially uniform width. The second set of struts 50, used for anchoring or mounting the filter, thus extends from tubular portion 18 and the first set of struts 30, used for filtering and additionally anchoring, extends from tubular portion 18. longitudinal struts 40 extend between tubular portions 18 and 19, thus connecting the two sets of struts (see FIG. 3) and are shown in FIG. 1 in a first configuration.

The collapsed configuration of filter 10 reduces the overall profile to facilitate delivery to the site. The diameter of filter 10 in the collapsed configuration is represented by reference D1 and preferably is about 2 mm and more preferably about 1.7 mm. Other dimensions are also contemplated. The filter is thus preferably dimensioned for insertion through a 6 French delivery system or 6 French catheter. The diameter or transverse dimensions of the filter in the expanded placement configurations is greater than the diameter or transverse dimension D1 in the collapsed (delivery) configuration.

FIGS. 3-5 illustrate the expanded placement configuration of the filter 10. As noted above, filter 10 has a first set of struts 30 forming a bell-shaped region in the expanded configuration. The struts 30 have a filtering region 32 having a converging region 34. At the opposing end, the struts 30 have a flared region 35. In larger vessels, the filter can expand to a diameter or transverse dimension shown in FIG. 4. In smaller vessels, the filter expands to a smaller diameter than in larger vessels. Diameters (or transverse dimensions) preferably range from about 18 mm to about 32 mm, depending on the internal diameter of the vessel wall as will be explained in more detail below. Other dimensions are also contemplated.

Struts 30 are spaced apart as shown and extend at an angle away from the longitudinal axis L of filter 10 in region 35 to provide a flare. Preferably, this angle or taper is about 10 degrees, although other dimensions are contemplated. In the filtering region 32, beginning at an intermediate portion of the filter (the transition between the regions 35, 32) the struts 30 extend inwardly to the longitudinal axis at an angle to the respective tubular portion 19 thereby forming an angle with the longitudinal axis. That is, filtering section 32 extends from the flared region toward the central longitudinal axis L of the filter 10 and converges at portion 34 into tubular portion 19. For clarity, not all of these sections of each strut 30 are labeled in the drawings, it being understood that the non-labeled struts have the same configurations.

Struts 50 are spaced apart as shown and extend at an angle preferably about 60 degrees (other dimensions are contemplated) away from the longitudinal axis L of filter 10. The struts 50 extend outwardly from the longitudinal axis at an angle to the tubular portion 18, thereby forming an angle with the longitudinal axis, and then curve outwardly at a lesser angle to provide mounting portions. The struts 50 are preferably flared. The struts 50 can have an elongated mounting surface to engage the vessel wall.

In the embodiment of FIG. 3, the struts 50 terminate in blunt tips 54. In this embodiment, the radial force of the struts 50 helps to retain the filter and helps prevent tilting and promote self-centering. In an alternate embodiment, the struts 50 can terminate in vessel engaging hooks. These are described below for example in the embodiment of FIG. 8, although such hooks can be placed on any of the filter embodiments described herein to enhance retention.

In the illustrated embodiment, when expanded, the six struts 50 and the six struts 30 are shown spaced approximately 60 degrees apart. It is also contemplated that a fewer or greater number of struts could be provided and spacing other than 60 degrees be provided. The struts 50 can also be radially offset from the struts 30, e.g., by 30 degrees. It is also contemplated that struts 50 can have a larger transverse dimension than struts 30.

In the expanded placement configuration, a portion of each elongated strut 30 and 50 has an outer surface 31, 51 respectively, for engagement with the vessel wall to help retain the filter 10 in position in the vessel. This region is angled with respect to the longitudinal axis. The outer surface 31, 51 of struts 30, 50 could be roughened to enhance engagement. Alternatively, a plurality of cutouts, atraumatic tabs, barbs or other penetrating members (not shown) can extend from the outer surface of one or more of the struts to engage the vessel wall to retain the filter.

As can be appreciated, the tubular portion 11 connects the struts 30 and 50. As shown in FIG. 3, two elongated struts 40 extend from tubular portion 18 to tubular portion 19, thereby connecting the regions 15 and 17. As shown in FIG. 3, the struts 40 remain in the same first configuration as in the collapsed configuration of FIG. 1, thus, not changing in configuration in delivery and placement. This can be achieved by removing some of the longitudinal struts during manufacturing. This reduces the amount of material, which is placed in the body. Alternatively, six longitudinal struts formed by the six cutouts could connect the regions 15 or 17, or a different number of struts could be provided.

With continued reference to FIGS. 3 and 4, each of the struts 30 terminates in a hook 60 which extends substantially perpendicular from the strut. This arrangement is achieved by torquing the struts 30 at the respective region 37 (or along an extended length of the strut) so the hook portions bend out of the plane. The hooks 30a, 30b of filter 10 lie in the plane of the end of the strut region, aligned with the width surface "w" of the region. The hooks can alternatively be formed or placed on fewer than all of the struts.

In the illustrated embodiment, the hooks of filter 10 in region 17 are of two different sizes. More specifically, a first set of hooks 60a is larger than a second set of hooks 60b. Preferably, when formed in a laser cut tube, hooks 60a are formed so that they occupy a region equivalent to the transverse dimension of two adjacent struts. For example, in the collapsed configuration, hook 60a occupies a region (dimension) of two struts while smaller hook 60b would only occupy the region (dimension) of one strut. Smaller hooks 60b are spaced axially inwardly with respect to larger hooks 60a to minimize the collapsed profile (transverse dimension) of the filter when collapsed for insertion. Hooks 60b are also preferably spaced axially with respect to each other. In this preferred embodiment, smaller hooks 60b occupy the space created by the larger hooks 60a so they can be considered as nesting within larger hooks 60a (see FIG. 2). Stated another way, each hook 60b has an outer surface 67 which conforms (follows the contour) to an inner surface 69 of a hook 60a. The penetrating tips 62a, 62b of hooks 60a, 60b, respectively, penetrate the tissue to retain the filter, preferably temporarily.

It should be appreciated that the hooks or other vessel engaging structure can be placed on both sets of struts 30, 50 or alternatively be placed only on struts 30 or only on struts 50 or placed on fewer than all the struts of the particular set of struts.

A recess or cutout can be provided at the tubular end portion 18 to receive a snare or other device for removal. In the preferred embodiment, a hook 92 at tubular portion 18 is illustrated and is configured to receive a snare.

Hook 90 has a curved hook 92 at the proximalmost end. Hook 92 is configured to receive a retrieval snare or other retrieval device. A portion of the wall of the hook 90 is cut out to expose the annular interior surface 94 (see FIG. 5B). That is, being formed from a laser cut tube, a wall portion is removed to expose curved inner wall surface 94. This annular interior surface 94 extends from radiused region 95 to proximalmost edge 96. The interior surface 94, for ease of explanation, can be considered to have an interior surface 94a at the radiused region 95 and an interior surface 94b at the hook 92. The interior surface 94b accommodates a portion of a tubular snare sheath. That is, the outer wall of the snare sheath (tube) can partially fit within the cut out region 93. This enhances removal as the snare pulls the filter hook into collinear arrangement with the sheath tube. The radiused region 95, spaced axially (distal) from the hook 92, includes a radiused or curved edge defined by radiused side walls 99a, 99c and a top wall 99b. The angled side walls 99a, 99c form camming surfaces to direct the hook 90 and filter into the retrieval sheath.

FIG. 6 illustrates an alternate embodiment of the filter of the present invention. In this embodiment, the struts of filter 100 are interconnected at the filtering region. This creates closed geometric shapes at the filtering region to enhance the clot capturing capability of the filter. Also, by providing the interconnection more forward (downstream) within the first region 112, i.e. in the filtering region (filtration zone), linear movement of the filter is facilitated to enhance removal of the filter.

Filter 100 has a filtering region (portion/section) 119 and a flared anchoring (mounting) region (portion/section) 121 in first region 112, forming a bell shape. The mounting region 121 is of greater transverse dimension than the respective filtering region 119. Flared region 121 is preferably at an angle of about 10 degrees with respect to the longitudinal axis of the filter, although other angles are contemplated. In this flared region 121, the transverse dimension increases towards the anchoring end of the region 112 so that as in the other embodiments disclosed herein, the end of the filter at region 119 has a smaller transverse dimension than at the opposing end at the respective flared regions 121. The filtering region 119 extends from the flared region 121 toward the longitudinal axis of the filter 100 and converges at portion 132 into tubular portion 129. Longitudinally extending struts 130 connect the two sets of axially spaced struts 114, 154. Providing fewer longitudinal struts 130 is also contemplated.

Filtering region 119 preferably has six struts 114 curving outwardly from tubular portion 129. Each filter strut or strut portion 114 extends radially from tubular portion 129 and divides into two connecting filter struts or strut portions 114a, 114b (preferably of equal width) that angle away from each other (in different directions) to extend to the connecting strut portion of an adjacent strut 114. Thus, connecting strut portion 114a of one strut 114 interconnects with the connecting strut portion 114b of an adjacent strut at joining or connecting region 114d. This forms closed geometric shapes 125, preferably substantially diamond shaped in configuration. For clarity, not all of the identical parts are labeled in the drawing. In the illustrated embodiment, preferably six struts are provided forming twelve interconnecting struts, however a different number of struts and closed geometric shapes can be provided. Also, fewer than all of the struts could be interconnected. Also, although preferably the struts 114 divide into connecting struts 114a, 114b of half the width of the undivided strut 114, the struts can bifurcate to form connecting struts of other dimensions. It is also contemplated that fewer than all of the struts can be interconnected.

After convergence of strut portions 114a, 114b at joining region 114d, it transitions into elongated mounting strut portions 114c which form flared mounting or anchoring region 121. The length of the strut portions 114c in the anchoring region 121 can vary, with increased/decreased length increasing the flexibility/rigidity of the struts. The thickness of the strut portions can also vary to affect flexibility/rigidity.

Struts 154 of filter 100 are preferably identical to struts 50 of FIG. 3. Thus, struts 154 extend outwardly from the longitudinal axis at an angle to the tubular portion 118 thereby forming an angle with the longitudinal axis, and then curve outwardly at a lesser angle to provide mounting portions. The struts 154 are preferably flared and have blunt ends 153.

Preferably, the strut portions 114c terminate in hooks 140a, 140b identical to hooks 60a, 60b of FIG. 3. That is, the hooks lie in the plane of the respective struts 114c and hooks 140a are larger than hooks 140b. The larger hooks are formed so they occupy a region equivalent to the transverse dimension of two adjacent struts. Smaller hooks 140b nest within larger hooks 140a as described above in conjunction with hooks 60a, 60b. Note that smaller hooks 140b are spaced axially (inwardly) of hooks 140a as well as spaced axially with respect to each other as in hooks 60b. Other hook designs could alternatively be provided. Struts 154 could also optionally terminate in hooks similar to hooks 140a and/or 140b (or other vessel engaging structure) instead of blunt tip 153 as in the embodiment of FIG. 8 described below.

Filter 100 can also preferably have a retrieval hook, such as hook 115 formed in tubular portion 118 which is identical to hook 92 of FIG. 1.

FIG. 7 illustrates another alternate embodiment of the filter, designated by reference numeral 200. Filter 200, having a first set of struts 214 and a second set of struts 234, is similar to filter 10 except for filtering region 219. That is, like filter 10, filter 200 has a filtering region 219, which extends from the flared anchoring region 221 and extends toward the central longitudinal axis of the filter 200, with struts 214 converging at portion 222 into tubular portion 231. The flared region, as in filter 10, is at an angle preferably about 10°, although other angles are contemplated. Struts 234 are identical to struts 154 of FIG. 6 and preferably have blunt tips 235. For clarity, not all of these sections of each strut 214, 234 are labeled in the drawing, it being understood that the non-labeled struts have the same configurations. Filter 210 preferably has a retrieval hook, such as hook 250, which is identical to hook 92 of FIG. 1, although other hooks are contemplated.

The region 219 of filter 200 where the struts 214 interconnect (join) differs from filter 100. In filter 200, the struts 214 bifurcate into connecting strut portions 214a, 214b that angle away from each other. The connecting struts are joined to connecting struts of adjacent struts at joining region 223. Thus, closed geometric shapes 228 are formed as shown. Six such closed geometric shapes 228 are preferably formed, each connecting adjacent struts, although fewer closed shapes are contemplated if fewer than all the struts are interconnected. Thus, stated in other words, as in the embodiment of FIG. 6, each strut 214 bifurcates or divides into two connecting strut portions 214a, 214b which initially extend outwardly from each other. As each strut extends outwardly, the strut portion 214a joins the strut portion 214b of an adjacent strut at region 223. However, after convergence of strut portions 114c, 114d at joining region 223, it bifurcates into connecting strut or strut portions 214c, 214d that angle away from each other. Connecting struts 214c, 214d of adjacent struts are joined at region 224, thus forming six closed geometric shapes 226. Strut portions 214c extend from joined region 224 and transition into hook regions and terminate in hooks 229a, 229b, preferably identical to hooks 60a, 60b of FIG. 3.

Although shown divided into equally dimensioned struts, as with the other embodiments described herein, the struts can bifurcate into connecting struts of varying dimension.

In the alternate embodiment of FIG. 8, filter 200' is identical to filter 200 of FIG. 7 except for the provision of hooks 270a, 270b on struts 234'. These hooks 270a, 270b provide additional retention of the filter 200'. The hooks 270a, 270b are preferably identical to hooks 229a, 229b, respectively of FIG. 7. Since the other features are identical to filter 200, corresponding parts are provided with "prime" designations. For clarity, not all parts are labeled.

Note the designations of longitudinal, angled, connected, joined connecting strut, interconnected, etc. in the illustrated embodiments described herein refer to the same integral strut and are divided into such regions for ease of understanding.

In the placement (expanded) configuration, the filter of the present invention moves towards its memorized position and the extent it returns to its fully memorized position will be dependent on the size of the vessel in which the filter is inserted. (The larger the vessel, the closer the filter comes to returning to its fully memorized position.)

To enable movement between an expanded and collapsed configuration, the filter tube of the embodiments described herein is preferably made of shape memory metal material, such as Nitinol, a nickel titanium alloy, or elgiloy. The memorized configuration of the filter 10 is shown in FIG. 3. To facilitate passage of the filter 10 through the lumen of the delivery sheath 100 (shown in FIG. 9 in conjunction with the method of insertion) and into the vessel, cold saline is injected into the delivery sheath or catheter 100 and around the filter 10 in its collapsed position within the delivery sheath 100. This shape memory material characteristically exhibits rigidity in the austenitic state and more flexibility in the martensitic state. The cold saline maintains the temperature dependent filter 10 in a relatively softer condition as it is in the martensitic state within the sheath. This facilitates the exit of filter 10 from the sheath 100 as frictional contact between the filter 10 and the inner surface of the sheath would otherwise occur if the filter was maintained in a rigid, i.e. austenitic, condition. Once ejected from the delivery sheath or catheter 100, the filter is no longer cooled and is exposed to the warmer body temperature, which causes the filter 10 to return towards its austenitic memorized configuration. Filters 10, 100, 200 and 200' operate in the same manner.

In alternate embodiments of the foregoing filters, the strut width can vary. For example, the struts can be wider at the flared region than at the filtering portion. This is preferably achieved by removing material to create the thinner portions. These thinner portions increase the flexibility of the filter for forming the angled and curved portions upon deployment. Alternatively, the filter can have struts which are thinner, rather than wider, at the flared region than at the angled and curved regions of the filtering portion. This would provide more stability at the curved regions. The adjustment of the widths is designed to strike a balance between stability and flexibility of the various regions of the filter. Thus, other width variations are contemplated such as making multiple width changes within each strut and/or in different struts.

The filter 10 (and other filters described herein) can be inserted through the jugular vein in the neck of the patient or through the femoral vein in the leg of the patient or the arm. The filters can also be placed in the superior vena cava. It can also be removed from access through the inferior vena cava or through the internal jugular vein.

FIGS. 9-11 illustrate delivery and placement of the filter 10, by way of example, in the inferior vena cava. Delivery catheter 100 is inserted through the femoral vein "f" and advanced through the iliac arteries into the inferior vena cava. Delivery catheter would be withdrawn once the tip of the sheath is adjacent the structure so that withdrawal of the sheath would place the filter in the desired location of FIG. 11. Tubing 104 and valve assembly 106 enable saline injection. Delivery catheter 100 is withdrawn to enable filter 10 to be warmed by body temperature to transition to the expanded placement configuration. The other filters described herein could be inserted in the same manner. This enables blood clots or other particles to be directed to the center of the filter section by the angled struts. Thus the direction of insertion, e.g. upstream or downstream direction, will determine how the filter is to be positioned in the delivery catheter.

To facilitate removal of the filter from the vessel, cold saline can be injected onto the implanted filter or within the retrieval sheath to change the temperature of the filter to move it to a relatively softer condition to facilitate the filter being drawn into the retrieval sheath. That is, injection of cold saline will cause the filter to approach its martensitic state, bringing the filter to a more flexible condition. The flexible condition facilitates the collapse and withdrawal of the filter into the retrieval sheath by decreasing the frictional contact between the filter and the inner surface of the retrieval sheath.

While the above description contains many specifics, those specifics should not be construed as limitations on the scope of the disclosure, but merely as exemplifications of preferred embodiments thereof. For example, the filters can be inserted in other regions of the body. Also, any of the aforedescribed filters can have mounting sections of varying thickness. The foregoing filters can be made of materials other than shape memory material. Those skilled in the art will envision many other possible variations that are within the scope and spirit of the disclosure as defined by the claims appended hereto.

What is claimed is:

1. A vessel filter comprising a first region and a second region, the filter movable between a collapsed position for delivery to the vessel and an expanded position for placement within the vessel, the first region having a first set of struts forming a first mounting portion and a first filter portion opening in a first direction, the filter portion having a first converging region at a first portion to direct particles toward the center of the filter, the mounting portion being flared in the expanded position to have a transverse dimension increasing toward a second portion opposite the first portion, the second region having a second set of struts forming a second mounting portion being flared in the expanded position and opening in the first direction, a plurality of spaced apart struts extending between the first and second regions and being substantially parallel to a longitudinal axis of the filter in the collapsed and expanded positions of the filter and remaining in the same configuration in the collapsed and expanded positions of the filter, the spaced apart struts having a proximal portion and a distal portion, the distal portion including a first tubular portion and the proximal portion including a second tubular portion, the second set of struts integral with and extending from the second tubular portion and the first set of struts integral with and extending from the first tubular portion.

2. The vessel filter of claim 1, wherein the filter is formed from a laser cut tube and composed of shape memory material.

3. The vessel filter of claim 2, wherein at least two adjacent struts of the first set of struts are interconnected by strut portions extending towards one another.

4. The vessel filter of claim 1, wherein struts of the first set of struts terminate in a vessel engaging hook.

5. The vessel filter of claim 4, wherein each of the vessel engaging hooks lies in a common plane with the respective strut.

6. The vessel filter of claim 1, wherein struts of the second set of struts terminate in a vessel engaging hook.

7. The vessel filter of claim 6, wherein struts of the first set of struts terminate in a vessel engaging hook.

8. The vessel filter of claim 1, wherein at least two adjacent struts of the first set of struts are interconnected by strut portions extending towards one another.

9. The vessel filter of claim 8, wherein the at least two adjacent struts interconnect at a first joining region and then bifurcate into two interconnecting struts, wherein interconnecting struts of adjacent struts join at a second joining region.

10. The vessel filter of claim 1, wherein the second region further includes a retrieval region, the retrieval region including a hook having a cutout exposing an internal annular surface, the annular surface dimensioned to receive a portion of a retrieval sheath.

11. The vessel filter of claim 10, wherein the retrieval region includes a radiused region having first and second curved surfaces extending distally inwardly.

12. The vessel filter of claim 1, wherein adjacent struts of the first set of struts are interconnected to form a series of closed cells in one region such that the number of closed cells corresponds to the number of first struts extending from the first tubular portion.

13. A vessel filter comprising a body cut from a tube, the body having a first integral region and a second integral region and being movable between a collapsed position for delivery to the vessel and an expanded position for placement within the vessel, the first region of the filter having a first set of spaced apart struts forming a first filter portion having a first converging region and a first mounting region for mounting the filter, the second region formed by a second set of spaced apart struts forming a second mounting region for mounting the filter, the second set of struts being positioned proximal of the first set of struts, the first and second set of struts being connected by a plurality of longitudinally extending struts and both sets of spaced apart struts being oriented in a first direction, the longitudinally extending struts being spaced apart to form longitudinally extending gaps therebetween formed by cuts in the tube, the longitudinally extending struts being substantially parallel to a longitudinal axis of the filter in the collapsed and expanded positions of the filter and remaining in the same configuration in the collapsed and expanded positions of the filter.

14. The vessel filter of claim 13, wherein adjacent struts of the first set of struts are joined by a connecting strut.

15. The vessel filter of claim 14, wherein struts of the second set of struts include vessel engaging members to enhance retention of the filter.

16. The vessel filter of claim 15, wherein struts of the first set of struts include vessel engaging members to enhance retention of the filter.

17. The vessel filter of claim 14, wherein struts of the first set of struts include vessel engaging members to enhance retention of the filter.

18. A vessel filter comprising a first region at a distal portion of the filter and a second region at a proximal portion of the filter, the filter movable between a collapsed position for delivery to the vessel and an expanded position for placement within the vessel, the first region having a first set of struts and having a first mounting portion and a first filter portion opening in a first direction and having a first converging region at a first portion to direct particles toward the center of the filter, the first converging region converging to a first tubular portion and the first set of struts extending integrally and distally from the first tubular portion, the first tubular portion positioned proximal of the first set of struts, the second region having a second tubular portion and a second set of struts extending integrally and distally from the second tubular portion, the second tubular portion positioned proximally of a proximalmost portion of the second set of struts, and adjacent struts of the first set of struts are interconnected by strut portions extending towards one another, in the collapsed position and expanded position a longitudinally extending set of struts having a first configuration extending longitudinally between the first and second tubular portions, the longitudinally extending set of struts remaining in the same first configuration in the collapsed and expanded positions of the filter.

19. The vessel filter of claim 18, wherein struts of the first set of struts terminate in vessel engaging members.

20. The vessel filter of claim 18, wherein adjacent struts of the first set of struts are interconnected to form a series of closed cells in one region such that the number of closed cells corresponds to the number of first struts extending from the first tubular portion.

* * * * *